US 7,766,946 B2

(12) United States Patent
Bailly

(10) Patent No.: US 7,766,946 B2
(45) Date of Patent: Aug. 3, 2010

(54) DEVICE FOR SECURING SPINAL RODS

(76) Inventor: Frank Emile Bailly, 939 Evening Shade Dr., San Pedro, CA (US) 90731

( * ) Notice: Subject to any disclaimer, the term of this patent is extended or adjusted under 35 U.S.C. 154(b) by 727 days.

(21) Appl. No.: 11/489,379

(22) Filed: Jul. 18, 2006

(65) Prior Publication Data
US 2007/0055242 A1 Mar. 8, 2007

Related U.S. Application Data

(60) Provisional application No. 60/703,321, filed on Jul. 27, 2005.

(51) Int. Cl.
*A61B 17/70* (2006.01)
*A61B 17/88* (2006.01)

(52) U.S. Cl. .................. 606/267; 606/279

(58) Field of Classification Search .......... 606/246, 606/264, 265, 267–270, 272, 279, 328; 60/60, 60/250–263, 266, 271, 273–279, 300–321; 411/554, 555, 400, 401, 380; 403/348, 349
See application file for complete search history.

(56) References Cited

U.S. PATENT DOCUMENTS

| 2,984,241 A | 5/1961 | Carlson |
| 4,188,952 A | 2/1980 | Loschilov et al. |
| 4,611,580 A | 9/1986 | Wu |
| 4,653,481 A | 3/1987 | Howland et al. |
| 4,658,809 A | 4/1987 | Ulrich et al. |
| 4,719,905 A | 1/1988 | Steffee |
| 4,763,644 A | 8/1988 | Webb |
| 4,805,602 A | 2/1989 | Puno et al. |
| 4,913,134 A | 4/1990 | Luque |
| 5,005,562 A | 4/1991 | Cotrel |
| 5,053,036 A | 10/1991 | Perren et al. |

(Continued)

FOREIGN PATENT DOCUMENTS

DE 9403231 U1 6/1994

(Continued)

OTHER PUBLICATIONS

English translation of DE 9403231 as cited in IDS from the European Patent Office. Pages 1-3.*

(Continued)

*Primary Examiner*—Eduardo C Robert
*Assistant Examiner*—Devanie Dufour
(74) *Attorney, Agent, or Firm*—Wean Khing Wong; Liu & Liu

(57) ABSTRACT

The present invention is directed to a device for securing a spinal rod to a fixation device such as a pedicle screw or a lamina hook. The device disclosed herein includes a head portion configured to receive a spinal rod, a locking cap configured to engage the head portion and the spinal rod upon rotation of the locking cap relative to the head portion to secure the position of the head portion and the locking cap relative to the spinal rod, and a fastener portion extending from the head portion and configured to engage the spine. The fastener portion of the device can be in the form of a screw, hook or clamp, or any other configuration known in the art.

26 Claims, 10 Drawing Sheets

U.S. PATENT DOCUMENTS

| | | | |
|---|---|---|---|
| 5,154,719 A | 10/1992 | Cotrel | |
| 5,207,678 A | 5/1993 | Harms et al. | |
| 5,257,993 A | 11/1993 | Asher et al. | |
| 5,306,275 A | 4/1994 | Bryan | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,534,001 A * | 7/1996 | Schlapfer et al. | 606/302 |
| 5,545,165 A | 8/1996 | Biedermann et al. | |
| 5,549,608 A | 8/1996 | Errico et al. | |
| 5,554,157 A | 9/1996 | Errico et al. | |
| 5,562,663 A | 10/1996 | Wisnewski et al. | |
| 5,586,984 A | 12/1996 | Errico et al. | |
| 5,667,508 A | 9/1997 | Errico et al. | |
| 5,672,176 A | 9/1997 | Biedermann et al. | |
| 5,725,527 A | 3/1998 | Biedermann et al. | |
| 5,733,286 A | 3/1998 | Errico et al. | |
| 5,752,957 A | 5/1998 | Ralph et al. | |
| 5,782,833 A * | 7/1998 | Haider | 606/266 |
| 5,797,911 A | 8/1998 | Sherman et al. | |
| 5,810,818 A | 9/1998 | Errico et al. | |
| 5,817,094 A | 10/1998 | Errico et al. | |
| 5,863,293 A | 1/1999 | Richelsoph | |
| 5,882,350 A | 3/1999 | Ralph et al. | |
| 5,885,286 A | 3/1999 | Sherman et al. | |
| 5,910,142 A | 6/1999 | Tartar | |
| 6,074,391 A | 6/2000 | Metz-Stavenhagen et al. | |
| 6,077,262 A | 6/2000 | Schlapfer et al. | |
| 6,090,111 A | 7/2000 | Nichols | |
| 6,113,601 A | 9/2000 | Tartar | |
| 6,132,432 A | 10/2000 | Richelsoph | |
| 6,139,549 A | 10/2000 | Keller | |
| 6,296,642 B1 | 10/2001 | Morrison et al. | |
| 6,302,888 B1 * | 10/2001 | Mellinger et al. | 606/270 |
| 6,454,773 B1 | 9/2002 | Sherman et al. | |
| 6,485,494 B1 | 11/2002 | Haider | |
| 6,488,681 B2 | 12/2002 | Martin et al. | |
| 6,520,963 B1 | 2/2003 | McKinley | |
| 6,540,749 B2 | 4/2003 | Schafer et al. | |
| 6,554,834 B1 | 4/2003 | Crozet et al. | |
| 6,565,565 B1 * | 5/2003 | Yuan et al. | 606/272 |
| 6,585,737 B1 * | 7/2003 | Baccelli et al. | 606/278 |
| 6,652,526 B1 * | 11/2003 | Arafiles | 606/308 |
| 6,736,820 B2 * | 5/2004 | Biedermann et al. | 606/308 |
| 6,827,719 B2 * | 12/2004 | Ralph et al. | 606/272 |
| 6,863,464 B1 * | 3/2005 | Niklaus | 403/341 |
| 2001/0012937 A1 | 8/2001 | Schaffler-Wachter et al. | |
| 2001/0023350 A1 | 9/2001 | Choi | |
| 2001/0025180 A1 | 9/2001 | Jackson | |
| 2002/0026193 A1 | 2/2002 | Barker et al. | |
| 2002/0082602 A1 | 6/2002 | Biedermann et al. | |
| 2002/0116001 A1 * | 8/2002 | Schafer et al. | 606/61 |
| 2002/0120272 A1 | 8/2002 | Yuan et al. | |
| 2002/0143341 A1 | 10/2002 | Biedermann et al. | |
| 2003/0023240 A1 * | 1/2003 | Amrein et al. | 606/61 |
| 2003/0100904 A1 * | 5/2003 | Biedermann | 606/73 |
| 2003/0125742 A1 | 7/2003 | Yuan et al. | |
| 2003/0199873 A1 | 10/2003 | Richelsoph | |
| 2004/0102781 A1 | 5/2004 | Jeon | |
| 2004/0102782 A1 | 5/2004 | Vercellotti et al. | |
| 2004/0138660 A1 * | 7/2004 | Serhan | 606/61 |
| 2004/0158247 A1 | 8/2004 | Sitiso et al. | |
| 2004/0236330 A1 | 11/2004 | Purcell et al. | |
| 2005/0038430 A1 | 2/2005 | McKinley | |
| 2005/0049588 A1 | 3/2005 | Jackson | |
| 2005/0080486 A1 | 4/2005 | Fallin et al. | |
| 2005/0177154 A1 * | 8/2005 | Moumene et al. | 606/61 |
| 2005/0215998 A1 * | 9/2005 | Donath | 606/61 |
| 2006/0004357 A1 * | 1/2006 | Lee et al. | 606/61 |
| 2006/0025767 A1 * | 2/2006 | Khalili | 606/61 |
| 2006/0079895 A1 * | 4/2006 | McLeer | 606/61 |
| 2006/0155278 A1 * | 7/2006 | Warnick | 606/61 |
| 2006/0247636 A1 * | 11/2006 | Yuan et al. | 606/61 |
| 2006/0264933 A1 * | 11/2006 | Baker et al. | 606/61 |

FOREIGN PATENT DOCUMENTS

| | | |
|---|---|---|
| DE | 19509332 C1 | 8/1996 |
| DE | 19542116 A1 | 5/1997 |
| EP | 01190678 | 9/1984 |
| EP | 0238667 A1 | 9/1987 |
| EP | 0456470 A1 | 8/1991 |
| EP | 0535623 A1 | 4/1993 |
| EP | 0776635 A1 | 8/1993 |
| EP | 0732081 A1 | 2/1996 |
| EP | 0885598 A2 | 12/1998 |
| EP | 0947174 A2 | 10/1999 |
| FR | 2674118 A1 | 9/1992 |
| FR | 2682280 A1 | 4/1993 |
| FR | 279645 A1 | 1/2001 |
| WO | WO87/05793 | 10/1987 |
| WO | WO91/01691 | 2/1991 |
| WO | WO9408527 | 4/1994 |
| WO | WO88/03781 | 6/1998 |
| WO | WO99/65415 | 6/1998 |
| WO | WO9825534 | 6/1998 |
| WO | WO9832386 | 6/1998 |
| WO | WO9812976 | 7/1998 |
| WO | WO9832386 | 7/1998 |
| WO | WO9834554 | 10/1998 |
| WO | WO00/19923 | 4/2000 |
| WO | WO2004/041100 | 5/2004 |

OTHER PUBLICATIONS

"ASTM F1717-04 Standard Text Methods for Spinal Implant Constructs in a Vertebrectomy Model," Abstract, ASTM International (2004).

"AMT Polyaxial Pedicle Screw System," product brochure, A.M. Technology, Inc., U.S.A.

* cited by examiner

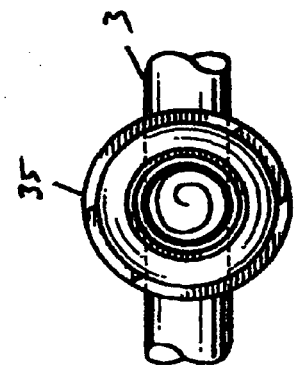
FIG.5
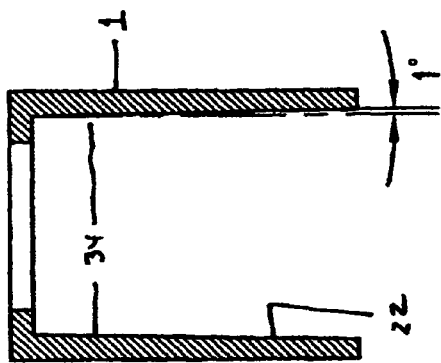
FIG.4C
FIG.4D
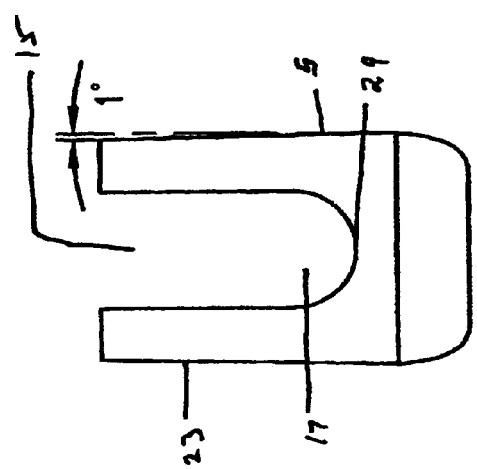
FIG.4B
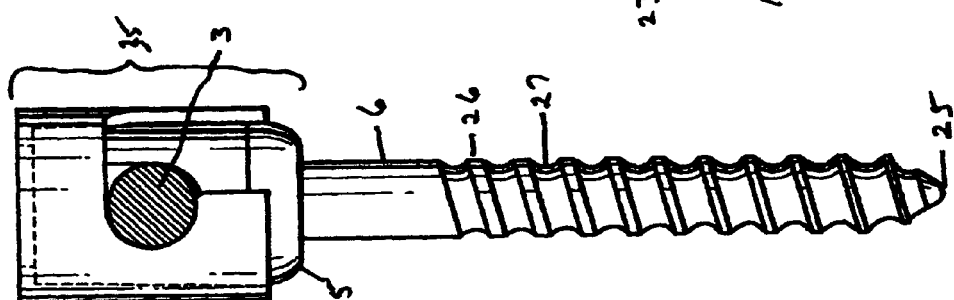
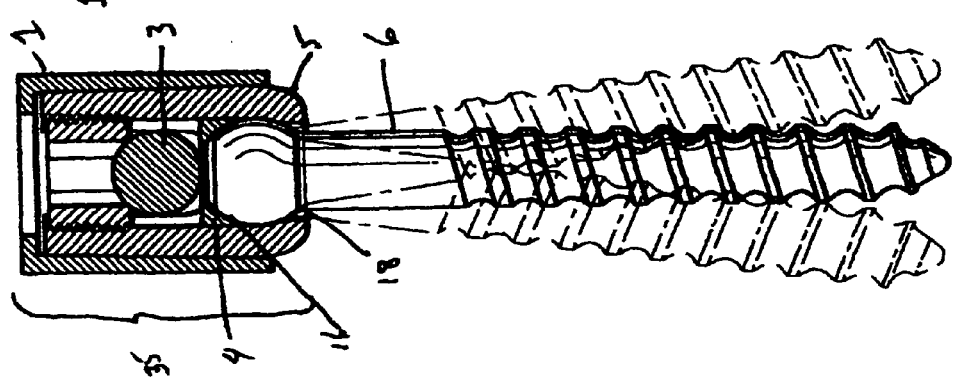
FIG.4A

DEVICE FOR SECURING SPINAL RODS

RELATED APPLICATION

This application claims the benefit of priority to Provisional Application No. 60/703,321, filed on Jul. 27, 2005.

All publications and patent applications cited herein are hereby incorporated by reference to the same extent as if each of them had been individually indicated to be incorporated by reference.

TECHNICAL FIELD

The present invention relates to implantable spinal stabilization systems for surgical treatment of spinal disorders, and more particularly, to a device for connecting spinal rods of a spinal stabilization system.

BACKGROUND OF THE INVENTION

Various methods of spinal immobilization have been known and used for many years to correct spinal irregularities, instability and displacement, in order to restore stability to traumatized areas of the spine. The preferred treatment for spinal stabilization is immobilization of the joint by surgical fusion, or arthrodesis. Spinal fixation is used, for example, to treat vertebral displacement and management such as kyphosis, spondylolisthesis and rotation; segmental instability, such as disc degeneration and fracture caused by disease, trauma, congenital defects, and tumors. It is found that immediate immobilization allows a bony union to form.

Spinal implant systems often include spinal instrumentation having connective structures such as round spinal rods which are placed on opposite sides of the portion of the spinal column intended to be immobilized. Fasteners such as screws and hooks are commonly utilized to facilitate segmental attachment of such connective structures to the posterior surfaces of the spinal laminae, through the pedicles, and into the vertebral bodies. These components provide the necessary stability both in tension and compression to achieve immobilization.

A concern of spinal fixation is where to secure the fixation device in the spine without damaging the spinal cord. The pedicles are usually chosen because they are strong enough to hold the fixation device even in patients with osteoporosis. Recently, posterior methods of fixation have been developed which use wires that extend through the spinal canal and hold a spinal rod against the lamina (such as the Luque system) or that utilize pedicle screws which extend into the pedicle and secure a plate which extends across several vertebral segments (such as the Steffee plate). A complete discussion of the various fixation systems are found in L. Wiltse, "Internal Fixation of the Lumbar Spine," *Clinical Orthopaedics and Related Research*, 203: 2-219 (February 1986). Known implant configurations include facet screws, double distraction systems, compression distraction systems, springs, spinous process plates, wired implants and transpedicular screw and plate systems. Examples of spinal fixation systems are described in, U.S. Pat. No. 5,443,467 (Biedermann et al); U.S. Pat. No. 5,474,555 (Puno et al); U.S. Pat. No. 5,752,957 (Ralph et al); U.S. Pat. Nos. 5,733,286 and 5,817,094 (both of Errico et al); U.S. Pat. No. 5,863,293 and 2003/0199873 (both of Richelsoph); U.S. Pat. No. 5,882,350 (Ralph et al); U.S. Pat. Nos. 5,885,286 and 6,454,773 (both of Sherman et al); U.S. Pat. Nos. 5,910,142 and 6,113,601 (both of Tatar); U.S. Pat. No. 6,488,681 (Martin et al); U.S. Pat. No. 6,485,494 (Haider); U.S. Pat. No. 6,520,963 (McKinley); U.S. Pat. No. 6,554,834 (Crozet et al); and U.S. Patent Application Pub. Nos. 2002/0120272 and 2003/0125742 (both of Yuan et al); 2004/0102781 (Jeon); 2004/0158247 (Sitiso et al); 2004/0236330 (Purcell et al); 2005/0038430 (McKinley); and 2005/0049588 (Jackson). U.S. Pat. No. 5,474,555 presents figures showing in detail how its spinal implant system is implanted in vivo. The commercially available spinal fixation systems (such as those from DePuy Orthopaedics, Inc., Interpore Cross International, and U&I Corporation) and some of those described in the foregoing patents and applications, have a generally U-shaped body into which a pedicle screw is inserted, either from the top or the bottom of the U-shaped body. A spinal rod is secured in the spinal rod passageway of the U-shaped body by various means.

Pedicle screws allow spine surgeons to attach spinal rods or plates to the thoracic and lumbar spine. This rigidly immobilizes the spine segments, promoting a bone graft to grow into a fusion, welding spinal segments into one solid unit, reducing pain and stabilizing deformity without requiring complete immobilization of the patient for the extended period of time during the healing process. For example, a spinal fixation system may be installed in patients who are receiving fusion by autogenous bone grafts and later removed after the grafts are successful.

While many different pedicle screws have been developed, presently most pedicle screws are fixed axis devices which must be carefully aligned during insertion and fixation in the spine. Specifically, the screws must be drilled or screwed into the bone at a very specific angle to assure that the alignment hardware is exactly positioned such that the receiving portions of the fixation hardware are aligned so that the spinal rod can be passed there through without distorting the screw or putting an undesirable level of stress on the attachment point. As a result, the alignment procedure requires a considerable amount of time, increasing the possibilities of complications during surgery and, in many cases the alignment fails and must be repeated. Further, the insertion of the screw is dependent on the angle of alignment required, resulting in insertions that are not in the most secure or safe positions with respect to the vertebral bodies.

The art contains a variety of pedicle screw fasteners which permit a level of freedom with respect to the alignment of the screw and the coupling element. However, these teachings have generally been complex, and inadequately reliable with respect to durability. The considerable drawbacks associated with the prior art systems include limited angular adjustability, complexity, difficulty of properly positioning the coupling elements and the spinal rod, tedious manipulation of the many parts associated with the complex devices and the considerable cost associated with manufacturing such complex mechanisms. Accordingly, a need exists for an inexpensive, durable and simple vertebral alignment assembly that allows a surgeon to freely manipulate the alignment of the coupling hardware such that the spinal rods can be properly positioned with respect to the pedicle screw and vertebral bodies without a time consuming and potentially dangerous alignment procedure. Also, it is known that threaded fasteners can become loosened under the influence of cyclically applied loads commonly encountered by the spinal column. Furthermore, during assembly, excessive torque applied to a threaded fastener can cause damage to the fastener as well as to the connective device with which it is associated. Therefore, a need exists for a more reliable and effective mechanism for facilitating the attachment of screws, hooks and clamps to the connective structures of a spinal stabilization system, while providing the surgeon a means to easily align the spinal rod with the pedicle screw assemblies, and allowing the surgeon to ensure that the spinal rod is aligned when implanting the pedicle screw assemblies, and allowing the spinal rod to stay aligned in relation to the pedicle screw assemblies in vivo.

SUMMARY OF THE INVENTION

The present invention is directed to a device for securing a spinal rod to a fixation device such as a pedicle screw or a lamina hook. The device disclosed herein includes a body configured to receive a spinal rod, a locking cap configured to engage the body and the spinal rod upon rotation of the locking cap relative to the body which secures the position of the body and the locking cap relative to the spinal rod, and a fastener portion extending from the body and configured to engage the spine. The fastener portion of the device for securing the spinal rod can be in the form of a screw, hook, clamp, wire, a spring or a plate or any other configuration known in the art.

The present invention is, also, directed to a method of spinal stabilization comprising attaching, to the spine or vertebrae of a patient in need thereof, a pedicle screw assembly for securing or fixing a spinal rod along a portion of the spine, wherein the pedicle screw assembly comprises a body portion that is preferably cylindrical in shape, which is configured to receive and hold a spinal rod, with a longitudinal central passageway and a vertical interior bore there through; a locking cap, for securing the spinal rod, configured to engage the body portion wherein the spinal rod rests; a fastener portion, which extends through the body portion through an opening in the lower end thereof and is configured to engage the spine, wherein the locking cap engages the body portion and the spinal rod upon rotation of the locking cap relative to the body which secures the position of the body and the locking cap relative to the spinal rod.

One advantage of the present invention is that it provides a method of spinal stabilization which permits a surgeon to easily and accurately ascertain that the spinal rod, being attached to the patient's spine or vertebrae, is properly aligned before finally fixing the pedicle screws into the vertebral bodies. This is accomplished by using a locking cap configured to engage the body and the spinal rod. Upon rotation of the locking cap relative to the body, the position of the body and the locking cap are secured relative to the spinal rod. The system includes a fastener portion extending from the body and configured to engage the spine. The locking cap will not engage the spinal rod and body portion when the spinal rod is not properly aligned with the pedicle screw assembly.

The few components of the present invention and the ease with which these components can be quickly assembled allow the surgeon to quickly assure that the spinal rods are in alignment while allowing the surgeon to freely adjust the angle of the pedicle screws with respect to the vertical axis of the body (See e.g. FIG. 4E). This is particularly important in the bloody environment which obscures the surgeon's manual access to and visual assessment of the spinal assemblies. Further, the present invention is an improvement over the previous spinal fixation systems because the present invention streamlines the surgical procedure and increases the ease of insertion and alignment, while maintaining the favorable attributes of the other systems. For example, the present invention has fewer parts and requires less time to implant than most of the previous screw and spinal rod systems. The present invention allows for adaptation to each patient's individual characteristics such as the degree of sagittal and/or coronal plane curvature, it also allows for safe and relatively risk-free insertion and manipulation of the spinal assemblies. At the same time, it allows the spinal rod to be aligned during the surgical operation and stay aligned after implantation and while in vivo (inside the patient). Whether the locking cap 1 is in position over body 5 and aligned with the spinal rod 3, or is locked into position (as shown in FIGS. 3, 11 and 12) can be easily ascertained by the surgeon either by feel or by sight.

BRIEF DESCRIPTION OF THE DRAWINGS

FIG. 4A is a sectional side view of the assembled pedicle screw assembly according to an embodiment of the invention showing the polyaxial movement of the pedicle screw with respect to the body.

FIG. 4B is an elevational side view of an embodiment of the assembled pedicle screw assembly according to an embodiment of the invention.

FIG. 4C is an enlarged sectional view of the locking cap 1 showing tapering of the internal surface of the locking cap in an embodiment of the pedicle screw assembly according to the invention.

FIG. 4D is an enlarged sectional view of the body 5 showing tapering of the external surface of the body in an embodiment of the pedicle screw assembly according to the invention.

FIG. 5 is a bottom plan view of an embodiment of the assembled pedicle screw assembly according to the invention.

DETAILED DESCRIPTION OF THE INVENTION

Figure 3:
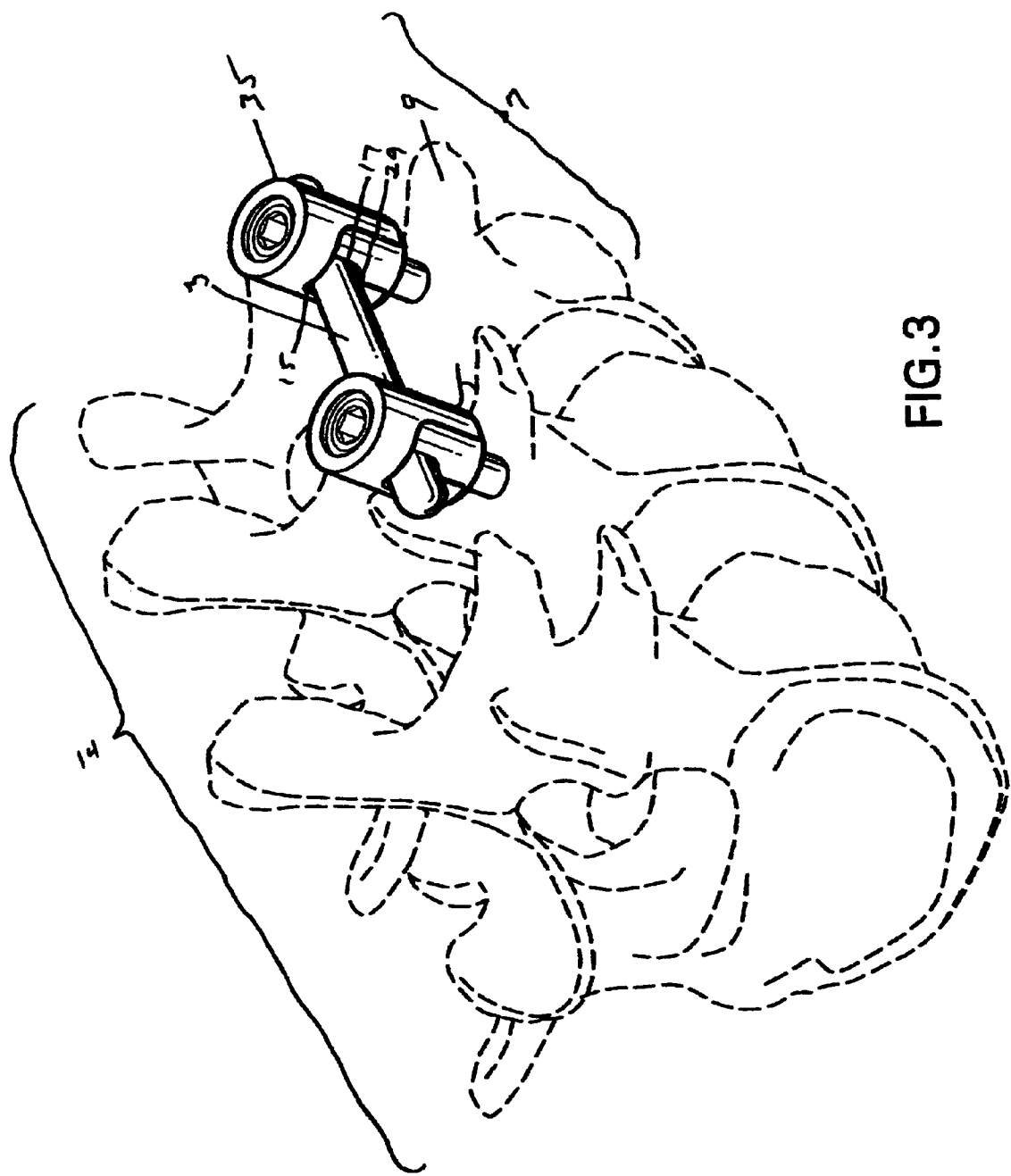
FIG. 3 is a schematic view of the alignment of the spine utilizing an embodiment of the spinal fixation system according to the invention.
Figure 11:
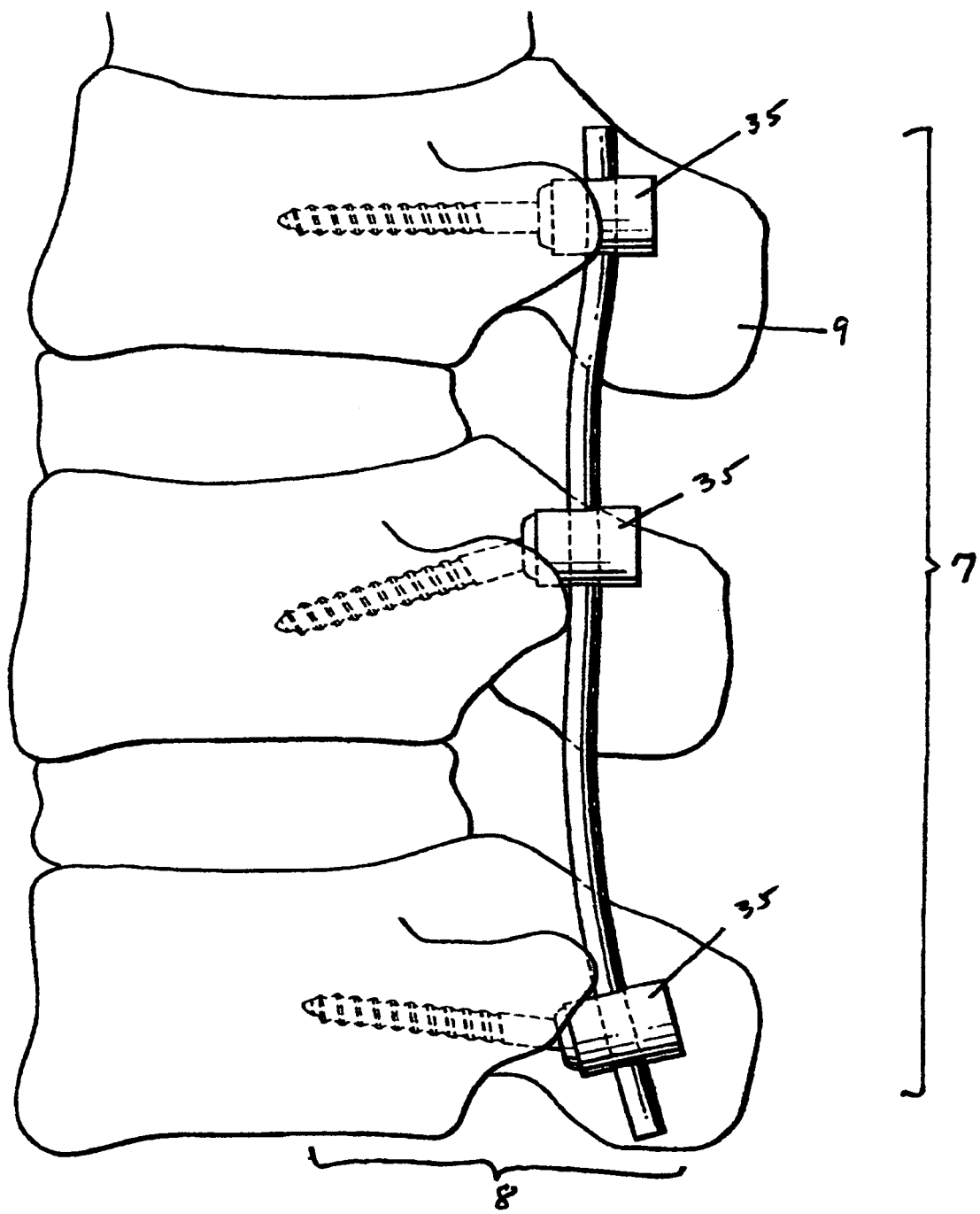
FIG. 11 is a side view of an embodiment of the instant spinal fixation system illustrating a correctly aligned spinal rod with the pedicle screw assemblies fastened to adjacent vertebrae.
Figure 12:
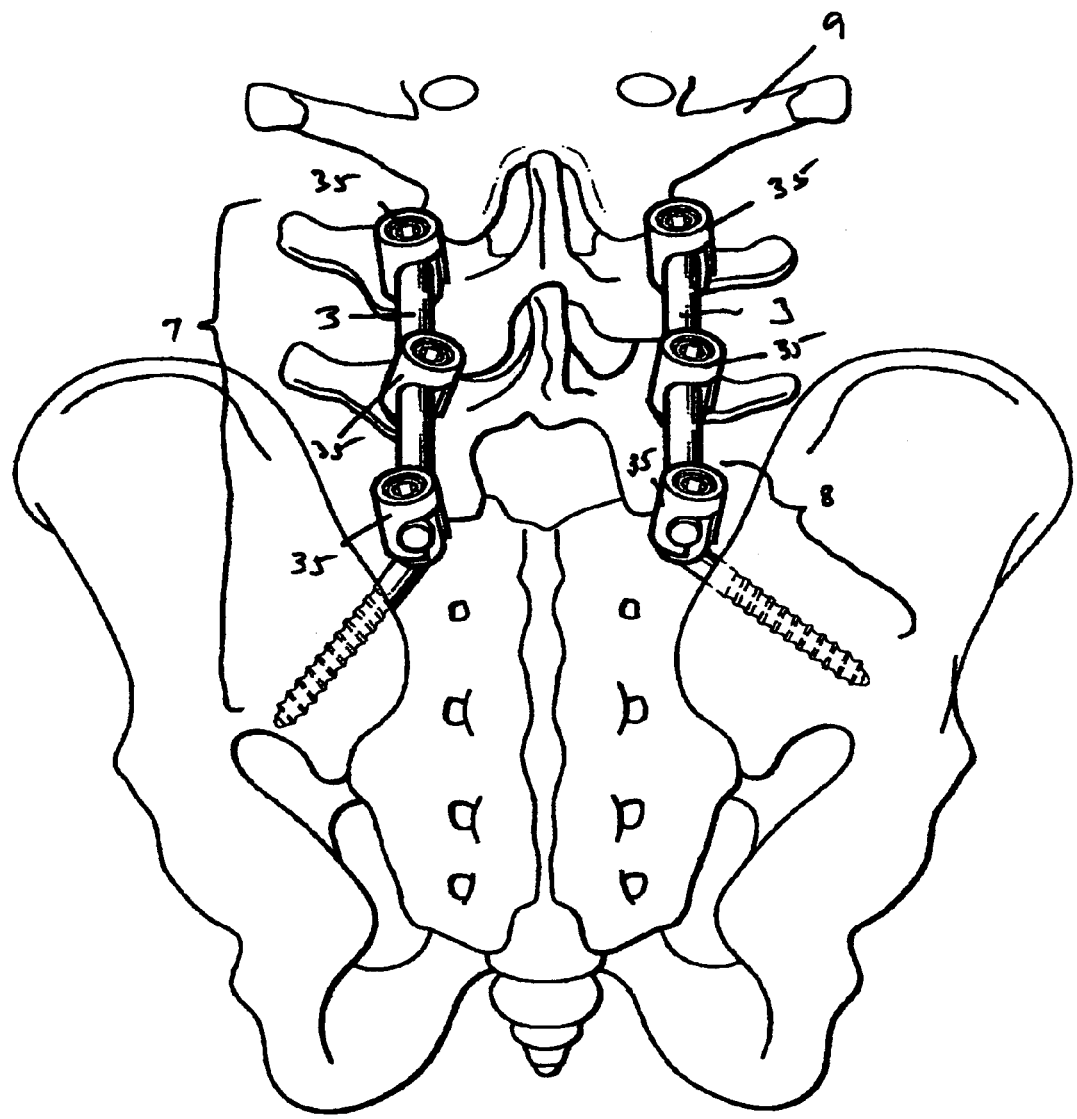
FIG. 12 is a top view of an embodiment of the instant spinal fixation system illustrating two rows of pedicle screw assemblies where each row includes a correctly aligned spinal rod with the pedicle screw assemblies fastened to adjacent vertebrae.

The present invention's method and device allow a surgeon to determine the alignment and to ensure the alignment of the spinal rod with respect to the pedicle screw assemblies 8, as shown in FIGS. 3 and 12, before finally fixing the pedicle screws into the vertebral bodies. The alignment of the spinal rod is assisted by the locking cap 1. If the spinal rod is not aligned, the locking cap will not lock, this will alert the surgeon to readjust the position or location of one or more pedicle screw assemblies, or to remove the spinal rod and bend it, and to re-insert it and re-test for alignment using the locking cap 1. The locking cap 1 also ensures that the spinal rod remains aligned in vivo after surgery (see FIGS. 11 and 12). Further details are discussed below.

As shown in the FIGS. 11 and 12, one embodiment of the present invention is a spinal fixation system 7 comprising two or more pedicle screw assemblies 8, which immobilizes and stabilizes vertebral bodies. The preferred embodiment is a polyaxial spinal fixation system 7, as shown for example in FIGS. 11 and 12.

With reference to the figures, typically, all components of the spinal fixation system 7 are comprised of materials traditionally used for spinal fixation (such as the pedicle screw 6 and spinal rod 3) which are biocompatible metals or alloys that provide sufficient strength and fatigue properties, such as cobalt chrome alloys, titanium and titanium alloys (such as Ti6Al4V ELI), and stainless steels. (See FIGS. 1A and 1B). The spinal rod used may be of any desirable shape or useful shape known in the field. Such shapes would include rods that are hexagonal, square or triangular and most preferably round or cylindrical.

Figure 1A:
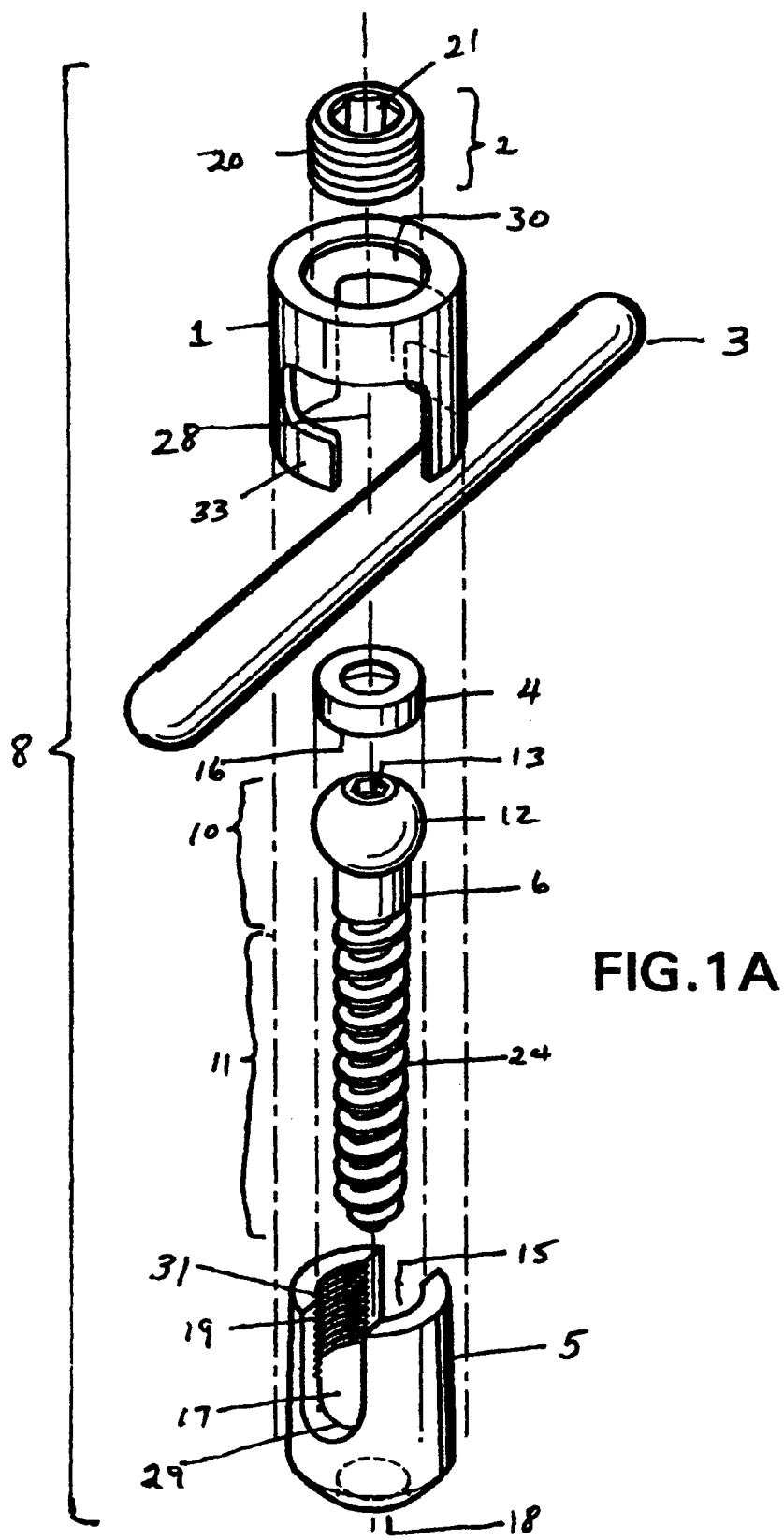
FIG. 1A is an exploded perspective of the pedicle screw assembly, according to an embodiment of the invention.

As shown in FIG. 1A, the pedicle screw assembly 8 is comprised of a pedicle screw 6 having an upper head portion 10 and a lower threaded portion 11 extending downwardly there from the head portion 10 includes a generally rounded or spherical enlarged head 12. A drive feature 13 is formed in the enlarged head 12, typically a hex depression for insertion of an Allen wrench or similar driver in order to drive the pedicle screw 6 into the vertebra 9 or other part of the spine 14, as shown in FIG. 3. The threaded portion 11 of the pedicle screw 6 extends through an opening 18 at the base of the body 5, as shown in FIG. 1B.

The drive feature 13, as shown in FIG. 1A, discussed above is an internal hex. However, any shape of drive feature 13 that transmits the loads necessary to drive the pedicle screw 6 into the vertebra can be formed on the enlarged head 12 of the pedicle screw 6. The drive feature 13 may be an internal drive feature such as the hex socket shown in this embodiment, or an external drive feature with geometry on the periphery of the enlarged head 12 of the pedicle screw 6 that engages with a corresponding internal drive feature on a driver tool (not shown). The specific shape of the drive feature 13 is dependent on the mating shape of the driver (not shown). Preferably, the drive feature 13 is of a polygonal, and typically hexagonal, exterior circumferential conformation so as to be received within a socket wrench or the like.

In the embodiment shown on the figures, the depth of the pedicle screw 6 is longer than its cross-section is wide. However, this depth and the foregoing respective proportion can be adjusted based on the material properties of the pedicle screw 6 and the drive tool (not shown).

Figure 1B:
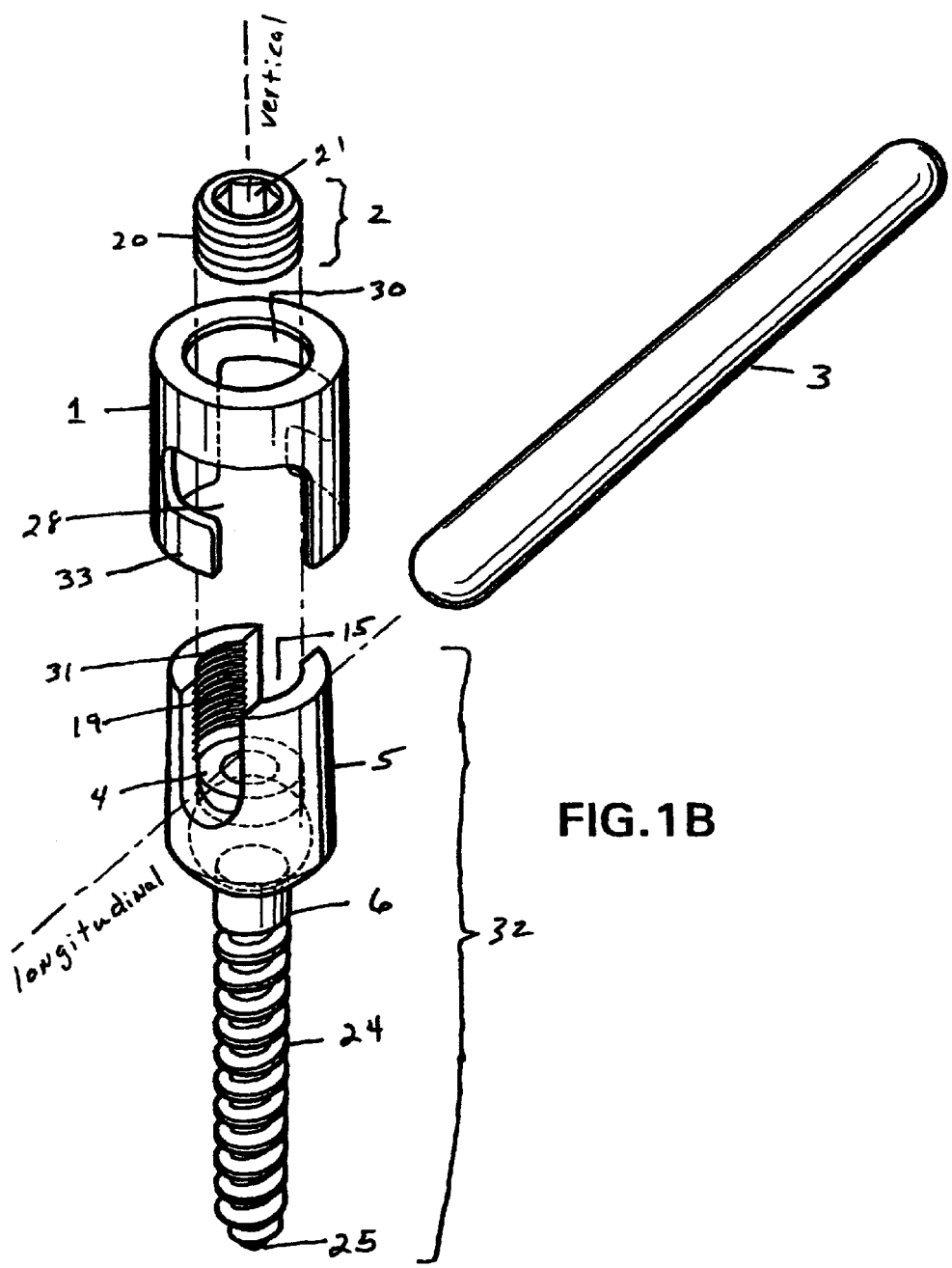
FIG. 1B is an exploded perspective of a partially assembled pedicle screw assembly according to an embodiment of the invention.
Figure 2:
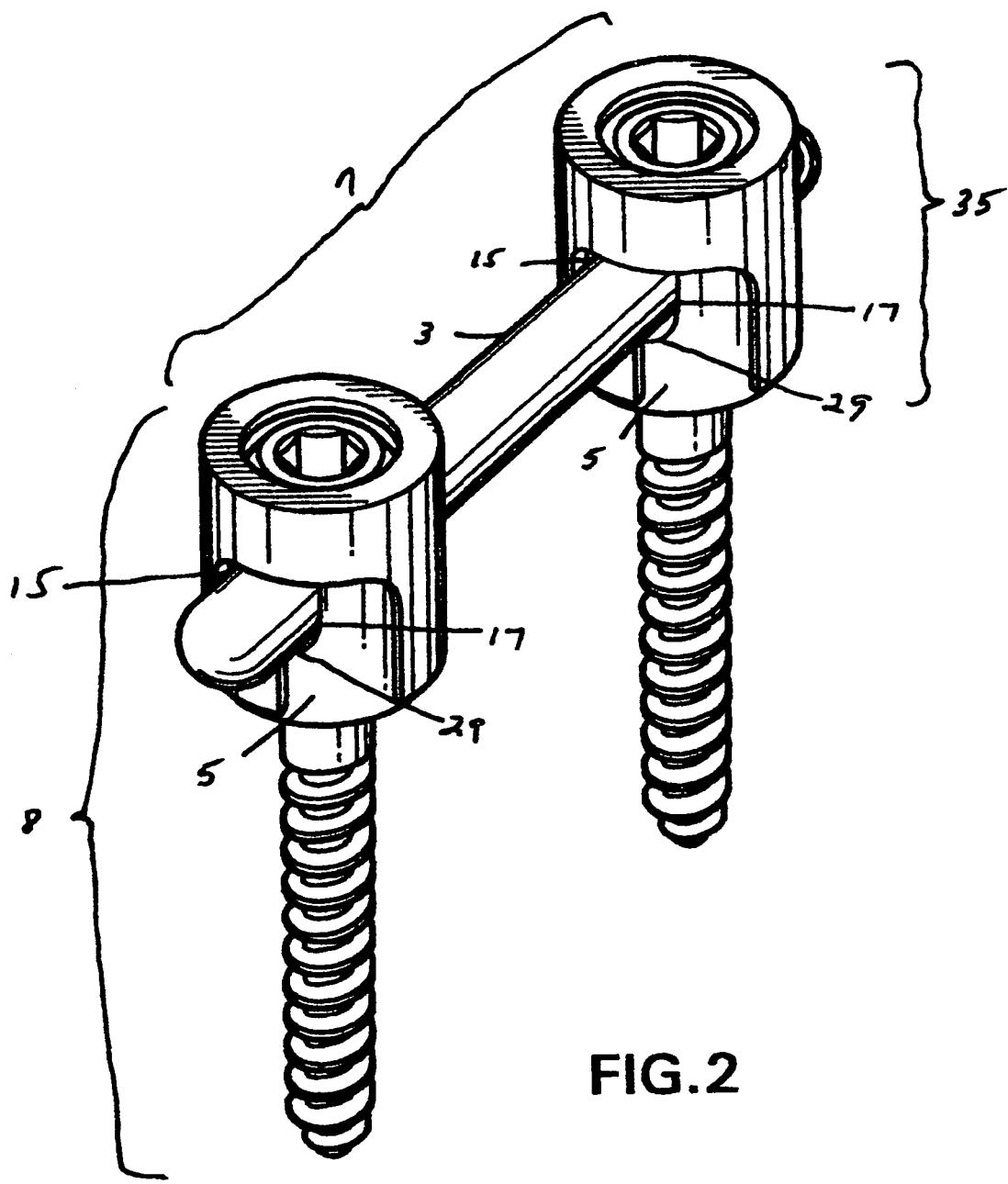
FIG. 2 is an assembled perspective of an embodiment of the use of the pedicle screw assembly of the invention in the spinal fixation system. In this figure, two pedicle screw assemblies are shown, connected by one spinal rod.
Figure 4E:
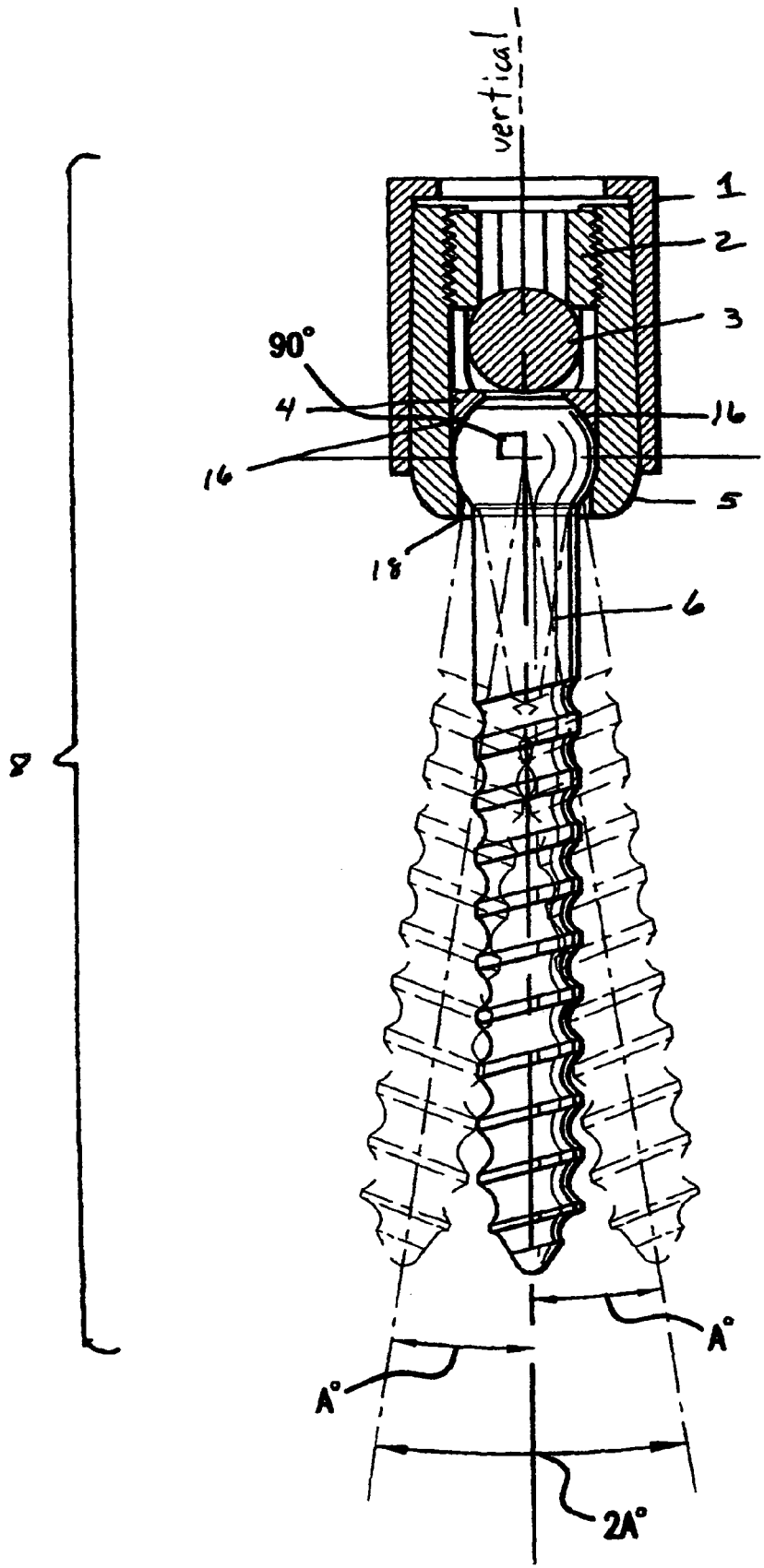
FIG. 4E is the same as FIG. 4A, but with the added markings to show angles A° and 2A°.

The body 5 has an vertical interior bore 15 as shown in FIGS. 1A and 1B with an opening 18 at the base of the body 5 which is configured so as to allow the lower portion of the pedicle screw to pass there through, but to prevent the enlarged head 12 of the pedicle screw from passing there through. The opening 18 is preferably defined by a concave rim, as illustrated in FIGS. 4A and 4E. In FIG. 1B, the line marked "longitudinal" indicates the longitudinal central axis of the body portion and the orientation of the spinal rod to the rest of the assembly, while the line marked "vertical" indicates the vertical axis of the body and exemplifies the position or relationship of those features which will be oriented at a 90° angle to the spinal rod when inserted into the body portion. FIG. 4E, also, indicates the vertical axis of the pedicle screw assembly 8. The spinal rod 3 is to be located in the spinal rod passageway 17 in a longitudinal orientation in relation to the body portion 5.

In a particularly preferred embodiment, a convex cap 4 is press fit into the vertical interior bore 15 of the body 5, wherein the convex cap 4 rests on the enlarged head 12 of the pedicle screw 6, and within the lower portion of the body 5 as shown in FIGS. 1A, 1B, 4A and 4E.

The preferred embodiment of the invention is a polyaxial spinal fixation system, with the different components (see e.g., FIGS. 1A and 4E), which the surgeon assembles together during an implant operation. In contrast, a monoscrew is a monolithic unit, in which, usually, the body 5 and the pedicle screw 6 are one unit or fused into one unit. This is unlike the polyaxial spinal fixation system, in which the pedicle screw 6 is a separate component from the body 5, and thus the pedicle screw 6 can pivot polyaxially, as shown, for example, in FIGS. 4A and 4E. In the preferred embodiment, the convex cap 4, has a generally concave facet 16 such that a spherical joint is created between the enlarged head 12 of the pedicle screw 6, the body 5 and the convex cap 4. (See FIGS. 1A, 4A, and 4E). This enables the body 5 and pedicle screw 6 to pivot and rotate with respect to one another. Typically, such degree of pivoting is approximately 15 degrees (angle A° as shown in FIG. 4E). This enables the pedicle screw 6 to be inserted into the bone while allowing the body 5 to polyaxially rotate and pivot somewhat for reception of a spinal rod, as illustrated in FIGS. 4A and 4E. The polyaxial pivoting action is discussed further below.

With particular reference to FIGS. 1A and 4D, the body 5 includes a spinal rod passageway 17, within the open-ended generally U-shaped slot 29 where the spinal rod rests after being inserted through the body portion 5. FIGS. 2, 3, 4A, 4E, and 5 illustrate the spinal rod 3 extending through the spinal rod passageway 17 of the body 5. The rod rests in the bottom of the U-shaped slot 29 of the body portion 5. (See FIG. 4D).

A compression device, such as a set screw 2, is sized and configured so as to be received within the upper entrance 30 of the locking cap 1, and the upper open end 31 of the body 5, as shown in FIGS. 1A, and 1B, In a preferred embodiment, the compression device is a set screw 2 having external threads 20 which are adapted to engage internal threads 19 present in the body portion 5, and wherein the opening in the top portion of the locking cap 1 will permit the set screw to pass there through, and wherein the set screw passes threadably through the vertical interior bore 15 of the body to engage the spinal rod that is present in the U-shaped slot 29, wherein the compression by the set screw holds the pedicle screw assembly 8 and the spinal rod 3 fixedly in place.

In a preferred embodiment as shown in FIGS. 1A and 1B, the upper portion of the body 5 includes internal threads 19. The set screw 2 has external threads 20 which are adapted to engage the internal threads 19 of the body 5. Preferably, the internal threads 19 and the external threads 20 are oppositely threaded. In one embodiment, the internal threads 19 of the body 5 are right hand threads while the external threads 20 of the set screw 2 are left hand threads. However, the right or left hand thread can be altered so long as the internal threads 19 and external threads 20 are oppositely threaded. The set screw 2 has a drive slot 21 formed therein for selective placement within the body 5. In one embodiment of the invention, the drive slot 21 is an internal hexagon configuration for engagement with a hexagon Allen wrench or driver.

The drive slot 21 discussed above may be an internal hex. However, one can use any shape of drive slot 21 that transmits the loads necessary to drive the set screw 2 onto the spinal rod 3. The drive slot 21 may be an internal drive slot such as the hex socket shown in this embodiment, or an external drive feature with geometry on the periphery of the set screw that engages with a corresponding internal drive feature on a driver tool (not shown). The specific shape of the drive slot 21 is dependent on the mating shape of the driver (not shown). Preferably, the drive slot 21 is of a polygonal, and typically hexagonal, exterior circumferential conformation so as to be received within a socket wrench or the like.

The figures show that threads 19, 20, and 24, are of the type American standard threads. However, threads 19, 20, and 24 may be of any type of threads, such as multiple lead threads, variable pitched thread, non-uniform pitch thread, buttress thread, Acme thread, or any other thread forms known in the art.

The locking cap 1 is sized and configured so as to be disposed over a top portion of the body 5. As shown in FIGS. 4C and 4D, the locking cap 1 includes a vertical internal wall 22 sized to receive the vertical external wall 23 of body 5. The opposing vertical walls of 22 and 23 may be straight. Alternatively, as illustrated in FIGS. 4A, 4B, 4C, and 4D, the vertical walls of 22 and 23 may be correspondingly tapered to allow locking cap 1 to mate with body 5. The tapering allows for a taper fit. Without tapering, a press fit is used. In FIGS. 4C and 4D, the angle of taper is illustrated at 1°. The tapering angle may be from about 1° to about 2°, or any degree of angle which allows the spinal fixation system to meet the applicable government regulatory and/or industrial standard. For example, the United States Food and Drug Administration and the United States orthopaedic industry has adopted ASTM F1717 (entitled "Standard Test Methods for Spinal Implant Constructs in a Vertebrectomy Model") as a benchmark for spinal implants. ASTM is the abbreviation for American Society for Testing and Materials. The current ASTM F1717 is that of the year 2004, and is designated ASTM F1717-04 (the "-04" denotes the year 2004). One skilled in the art may apply the ASTM standard(s) that is/are best suited for his use, such as the ASTM F1717 that is current as of the time of his use.

The locking cap 1 has a mechanical locking feature capable of locking the spinal rod 3 and the body 5 together. In one embodiment of the invention, as shown in FIGS. 1A and 1B, the locking feature is a mechanical interlocking fit in the form of a bayonet connection on locking cap 1, as shown in the figures, with a corresponding construction on body 5. The opposing bayonet connections have an opening 28 at opposing side of locking cap 1, into which the spinal rod may slide in at one opening and out the other opening. The opposing bayonet connections on locking cap 1 allow the locking cap 1 to lock the spinal rod into position in body 5 and stay locked, with the central axis of the spinal rod 3 (in the assembled locking cap 1 and body 5) being locked into a perpendicular position vis a vis the vertical axis of body 5, as shown in FIGS. 2, 3, 4A, 4B, 4E, 5, 6, 7, 11 and 12.

Once the locking cap 1 is locked into position with the spinal rod 3 extending through the spinal rod passageway 17 in body 5 and both the bayonet openings 28 of the locking cap 1, the user then screws the set screw 2 into body 5, by engaging the external threads 20 of set screw 2 with the internal threads 19 of body 5. See e.g., FIGS. 1B, 4A, 4B and 4E.

In use, the pedicle screw entry point is prepared in the spine structure, as is well-known in the art. In an embodiment of the present invention, the surgeon inserts the pedicle screw 6 (tail 25 down), as in FIG. 1B, through the opening 18 in the base of body 5 (See FIG. 1A), and then aligns the pedicle screw 6 with anatomic landmarks and drives (e.g., by applying an external driver, not shown, to the drive feature 13) the pedicle screw 6 into the spine 14 as seen in FIG. 3. That is, the enlarged head 12 of the pedicle screw 6 has a drive feature 13 shaped to accept a driver (not shown) that is used to drive an internal connection feature (e.g., lower threaded portion 11 of pedicle screw 6) into the spine 14. Usually, the pedicle screw 6 is fastened within the spine 14, with the head portion 10 remaining above the spine 14, as illustrated in FIG. 3. The same process is repeated for the adjacent vertebrae 9 of the spine 14. At this point, the pedicle screws are just loosely screwed in.

Some prior art systems used straight pedicle screws. However, it has been found that such screws can loosen over time and can self-remove, at least partially, from the spine structure. In one embodiment of the invention, in order to eliminate this possibility, the present invention utilizes a tapered lower thread portion 11 of the pedicle screw 6. That is, the major outer diameter 26 of the threaded portion is generally constant in diameter, while the inner minor diameter 27 of the pedicle screw 6 is increasingly tapered from the head portion 10 to the tip 25 of the pedicle screw 6, as illustrated in, for example, see FIG. 1A and FIG. 4B. This creates a thread taper which serves to securely lock the pedicle screw 6 in place within the spine 14.

In the operation room, the surgeon generally would be provided with a partially pre-assembled unit 32 (as shown in FIG. 1B) which consists of the pedicle screw 6, body 5, and the convex cap 4 which rests on the enlarged head 12 of the pedicle screw 6. The way these parts are assembled is shown in FIGS. 1A and 1B. That is, the lower threaded portion 11 of the pedicle screw 6 is passed through body 5, and the enlarged head 12 of the pedicle screw 6 rests inside body 5, and the concave surface 16 of convex cap 4 is placed on top of the enlarged head 12. The surgeon then loosely fastens this partially pre-assembled unit 32 into the vertebra. As an illustration, to arrive at the arrangement shown in FIG. 3, two partially pre-assembled units 32 are loosely fastened in place in adjoining vertebrae. As illustrated in FIG. 3, a spinal rod 3 is then extended through the spinal rod passageways 17 of the adjoining bodies 5, which extend above the vertebral bone. Due to the pivoting nature of the body 5 with respect to the pedicle screw 6, the body 5 and the pedicle screw 6 can be pivoted polyaxially with respect to one another until properly aligned for insertion of the spinal rod 3 through the spinal rod passageway 17 of the body 5.

Once inserted through the passageway 17, the spinal rod 3 rests on the convex cap 4 which in turn is rested on top of the enlarged head 12 of the pedicle screw 6. When the spinal rod 3 is in position, locking cap 1 is placed over body 5. As shown on FIG. 1A, the locking cap 1 has two opposing bayonet openings 28 to allow the spinal rod 3 to pass there through. The surgeon rotates the locking cap 1, over body 5, until the spinal rod passes through the passageway 17 on body 5, and both of the bayonet openings 28 of the locking cap 1 (See, e.g., FIGS. 1A, 1B, 2, 3, 4A and 4B). The opposing flange 33, shown in FIGS. 1A and 1B, of the locking cap serves to hold the spinal rod 3 in place within the cap 1 and also serves to hold the cap 1 in place. This ensures that the spinal rod is well aligned and in contact with convex cap 4. Set screw 2 is then inserted through the opening in the upper portion 30 of the locking cap 1, and into body 5, until it contacts the spinal rod 3, as illustrated in FIG. 4A. The external threads 20 of the set screw 2, mates with the internal threads 19 of the body 5, as shown in FIGS. 1A, 1B, 4A and 4E.

Initially, the set screw 2 and locking cap 1 are somewhat loosely fastened onto the body 5. Also, the pedicle screw 6 is loosely fastened onto the spine 14. The foregoing loose fastening allows the surgeon to adjust all the components of the spinal fixation system 7 to optimize their positions on the spine 14, and to adjust the bayonet openings 28 of the locking cap 1 to ensure the spinal rod 3 passes through the spinal rod passageways 17 of bodies 5 and the bayonet openings 28 of the locking caps 1 of the adjoining pedicle screw assemblies 8. The surgeon can ascertain that the spinal rod is well aligned by the fact that the locking cap 1 has locked the spinal rod 3 and the adjacent bodies 5 into position, as illustrated in FIGS. 2, 3, 11 and 12. If the spinal rod 3 is out of alignment, the locking cap 1 will not be able to slide over body 5 or it will not sit stably on the body 5, nor will it lock the spinal rod 3 and body 5 into position. Whether the locking cap 1 is in position over body 5, or is locked into position, can be easily ascertained by the surgeon either by feel or by sight.

Once all the components of the spinal fixation system are aligned, the surgeon performs the final tightening in which the set screw 2 is turned to tighten the spinal fixation system 7 as seen in FIGS. 2, 3, 11 and 12. Locking cap 1 includes a central bore 34 through which the set screw 2 passes. The set screw 2 presses the spinal rod 3 down onto the convex cap 4 which in turn presses against the enlarged head 12 of the pedicle screw 6 to fixedly anchor the pedicle screw 6 at a vertical or inclined angle vis a vis the spine 14. In the preferred embodiment, the device (not shown) which tightened the set screw 2, also simultaneously forces the locking cap 1 over the body 5 (See FIG. 4C), causing the internal vertical wall 22 of the locking cap 1 to squeeze against the external vertical wall 23 of the body 5 and thus holding body 5 within locking cap 1, meanwhile the locking cap 1 also fixedly holds the spinal rod 3 at a 90° degree angle vis a vis the vertical axis of the body 5. Preferably, for the final tightening of the pedicle screw assembly 8, the set screw 2 and body 5 are simultaneously turned in opposing direction. This simultaneous opposite turning serves to counteract the torque forces experienced by the pedicle screw assembly 8 and the connected vertebral bone 9. This allows the pedicle screw assembly 8 to be tightened to a great degree without placing undue strain on the pedicle screw assembly 8 or the underlying vertebral bone 9 as shown in FIG. 3. FIGS. 2, 3, 6, 7, 11 and 12 also indicate the orientation of the spinal rod 3 to the assembled upper portion 35 of the pedicle screw assembly 8.

Figure 6:
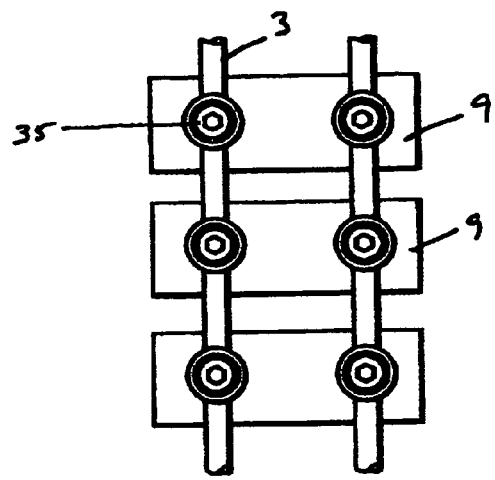
FIG. 6 is a schematic (representational) top view of an embodiment of the present pedicle screw assemblies, when implanted onto adjoining vertebra, illustrating proper alignment of the spinal rods along the vertebrae.
Figure 7:
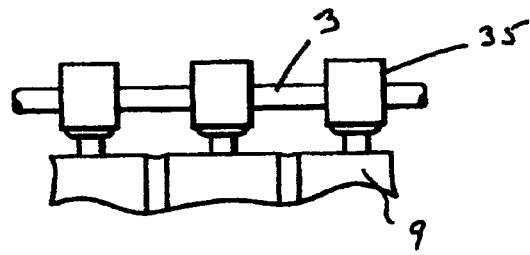
FIG. 7 is a schematic (representational) side view of an embodiment of the present pedicle screw assemblies, when implanted onto adjoining vertebrae, illustrating proper alignment of the spinal rods with respect to the pedicle screw assemblies.

The present invention is illustrated in FIGS. 3, 11 and 12, which show that the spinal fixation system 7 enables the spinal rods 3 to be fully aligned with the other components of the two adjacent pedicle screw assemblies 8, when implanted into adjacent vertebrae 9. The proper alignment of the spinal rods 3 in the pedicle screw assemblies when implanted onto adjoining vertebrae are schematically shown in FIGS. 6 and 7, and in FIGS. 11 and 12. FIG. 3 shows two pairs of pedicle screw assemblies 8 inserted into adjoining vertebrae 9 and interconnected by spinal rod 3. Although FIG. 3 illustrates two vertebrae which have been immobilized and stabilized by two pair of interconnected pedicle screw assemblies 8, it will be appreciated by those skilled in the art that three, four or even more vertebrae may be immobilized and stabilized with the use of additional pedicle screw assemblies 8 and longer spinal rods or additional spinal rods, see, e.g., FIGS. 6, 7, 11 and 12. In some instances, cross-linking members may be used to interconnect the generally parallel spinal rods 3, depending upon the need of each case and the desire of the surgeon. However, the spinal fixation system 7 of the present invention generally does not require such cross-links. On the other hand, the present invention allows for such cross-links, if the cross-links are necessary.

It will also be noted that FIG. 3 illustrates the spinal rod 3 as being generally straight. In prior systems, the spinal rods were required to be bent in order to interconnect the pedicles. However, in the present invention, the spinal rod 3 typically does not need to be bent, saving valuable surgical time. On the other hand, if needed, the spinal rod 3 of the present invention may be bent as desired by the surgeon or in certain complicated cases wherein several vertebrae are being fused together and immobilized by the spinal fixation system 7 of the present invention. It shall be noted that, even if the surgeon bends the spinal rod 3, the spinal rod may be pushed or pulled through the spinal rod passageway 17 of body 5 to adjust the spinal rod before finally screwing the pedicle screw assembly 8 into the vertebral bone 9. The locking cap 1 will assure that the central axis of the spinal rod 3 (in the assembled locking cap 1 and body 5) will be perpendicular to the vertical axis of body 5. However, the locking cap 1 will confirm to the surgeon as to whether the spinal rod is in alignment. If not, the surgeon will withdraw the spinal rod, bend it appropriately, and re-insert it to quickly and easily re-test for alignment, using the locking cap 1 as a guide, until the locking cap 1 confirms to the surgeon that the spinal rod is properly aligned (See e.g. FIG. 11). Thus, the invention ensures an alignment which hitherto has not been provided by the prior art.

That is, the locking cap 1 assures that the central axis of the spinal rod is perpendicular (aligned) to the vertical axis of the body 5, and therefore, the surgeon will achieve complete control over setting the angle(s) of the pedicle screw assembly or assemblies 8 between the vertebrae. In other words, the locking cap 1 assures that the part of the spinal rod which is inside both the bayonet openings of locking cap 1 is in contact with the set screw 2 and convex cap 4, and is perpendicular to the vertical axis of the body 5 (see e.g. FIGS. 3, 4E, 11 and 12). The locking cap 1 also allows the surgeon to easily and quickly assure that the spinal rod is aligned, since the locking cap 1 will not "lock" into position if the spinal rod is not aligned, or will not slide over body 5 or will not sit stably. That is, if the spinal rod is not aligned, it cannot both enter one bayonet opening 28 of the locking cap 1 (passing through the spinal rod passageway 17 of body 5) and exit the other bayonet opening 28 of the locking cap 1. Thus, if the spinal rod 3 is not aligned, the surgeon will easily find (by visual inspection or by feel) that the locking cap 1 will not slip over both the assembled spinal rod 3 and body 5, and will not lock the spinal rod into position. The locking cap 1 also allows the surgeon to determine the alignment of the spinal rod in the pedicle screw assembly 8, without using undue force. Thus, the surgeon can complete the implantation of the pedicle assemblies without unduly deforming the patient's vertebrae, and without causing harm and pain.

FIG. 6 provides a schematic (representational) top view of an embodiment of the present pedicle screw assemblies 8, when implanted onto adjoining vertebrae 9, illustrating proper alignment of the spinal rods 3 along the vertebrae. FIG. 7 provides a schematic (representational) side view of an embodiment of the present pedicle screw assemblies 8, when implanted onto adjoining vertebrae 9, illustrating proper alignment of the spinal rods 3 with respect to the pedicle screw assemblies.

Figure 10:
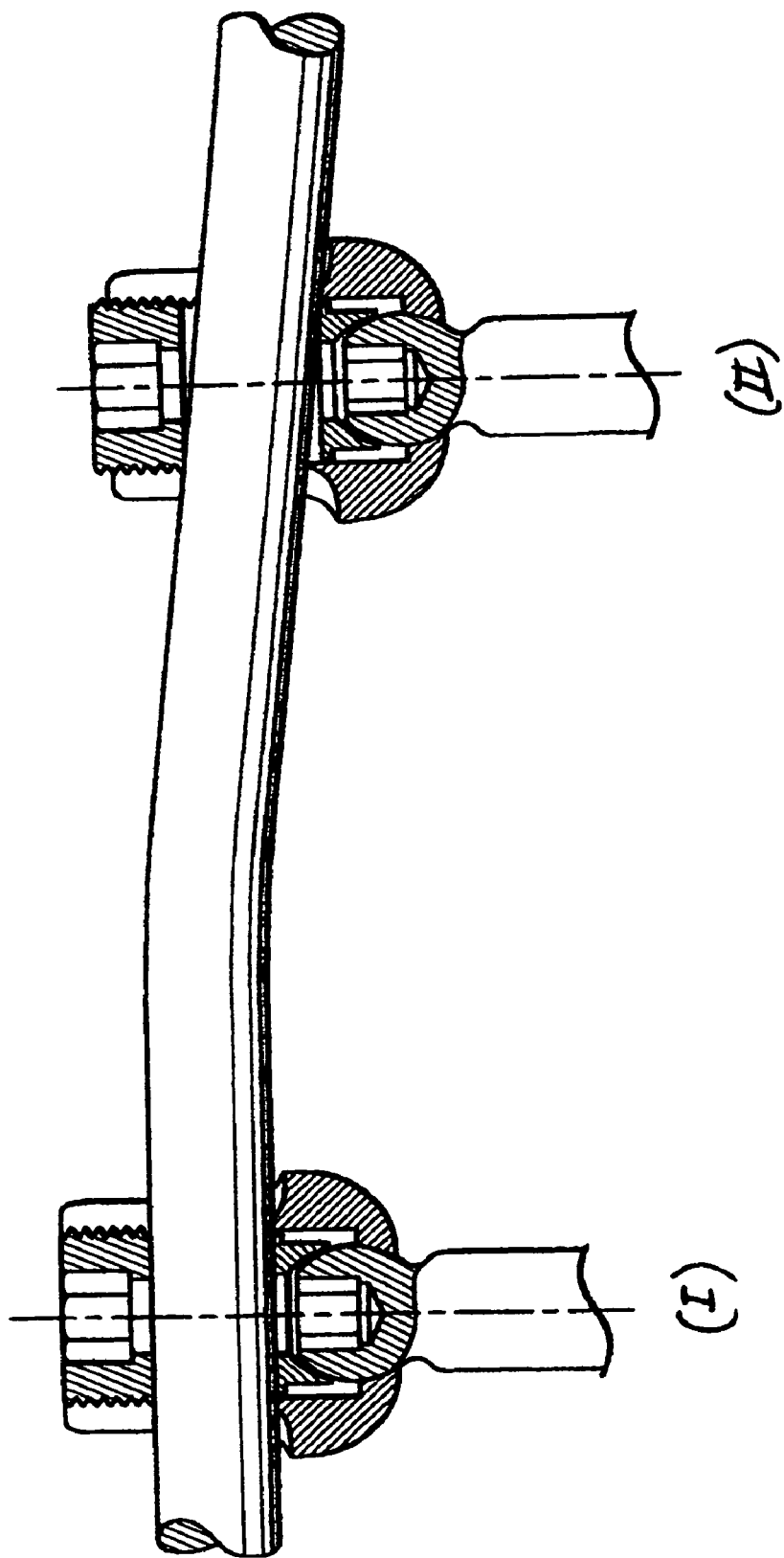
FIG. 10 is a side view of prior art pedicle screw assemblies, demonstrating the mis-alignment of the spinal rod in prior art.

In contrast, in the prior art spinal implant system, the surgeon may apply too much force in trying to tighten the set screw onto the spinal rod and onto the head of the pedicle screw, in order to ensure that the spinal rod is aligned within the pedicle assembly spinal implant system. Unfortunately, if the surgeon applies too much force, even though the alignment of the spinal rod may be assured, the prior art system suffers from the disadvantage that the greater force will deform the patient's vertebrae and thus cause harm and pain to the patient. On the other hand, if the surgeon does not apply increased force in tightening the set screw, the spinal rod may not be aligned within the pedicle assembly, as shown in FIG. 10 (Prior Art), wherein the prior art pedicle screw assembly consists of only a set screw, a washer and a body (such as in Jeon, U.S. published patent application 2004/0102781A1, published May 27, 2004). In FIG. 10 (Prior Art), for the sake of illustration, the prior art is shown with a spinal rod between a set screw and a washer. The pedicle assembly denoted with "(II)", in FIG. 10 (Prior Art), shows that when the set screw is loosely tightened (to avoid applying too much force and trauma to the vertebrae), the spinal rod may not be in full contact with both the set screw and the washer, such that the spinal rod is not aligned within the pedicle assembly. This is illustrated in FIG. 10 (Prior Art) in which two interconnected pedicle screw assemblies are shown: the spinal rod is aligned in the pedicle assembly denoted with "(I)"} but not in the pedicle assembly denoted "(II)". Even if the spinal rod is only out of alignment in one pedicle screw assembly, it causes instability in the network of pedicle screw assemblies connected, directly or indirectly, to the same spinal rod. Also, the non-aligned spinal rod undermines the surgeon's control over setting the angle of the pedicle screw assembly 8 between the vertebrae, and any other pedicle screw assemblies connected, directly or indirectly, with the non-aligned pedicle screw assembly.

Furthermore, typically in one embodiment of the invention, a polyaxial screw assembly allows the pedicle screw 6 to pivot polyaxially (in the x-, y-, z-axes) within an allowable degree. This is illustrated in FIG. 4E, wherein the maximum pivot angle is marked as "A°", relative to the central axis of the pedicle screw. Generally, the angle of pivot "A°" ranges from about 11 to about 26 degrees. For example, some polyaxial screw assemblies can pivot up to 11 degrees, some up to 13 degrees, and others up to 15 degrees or even up to 26 degrees. In one embodiment of the invention, the pivot angle "A°" is 14 degrees. Since angle "A°" is measured from the central axis of the screw, the maximum pivot angle "A°" is 14 degree to the left or right of the central axis of the pedicle screw in the pedicle screw assembly. This means that the total maximum angle of pivot "2A°" is 28 degrees (that is, the total maximum angle of pivot is "2A°" in a three-dimensional space, with the screw capable of moving within the circle shown in FIGS. 4A and 4E). FIGS. 11 and 12 illustrate the use of the pedicle screw assembly 8 where the polyaxial screw is in various pivotal positions relative to the central axis of the pedicle screw assembly 8. In FIG. 11, the polyaxial screws can be seen to be set into vertebrate 9 at different angles such as perpendicular as well as pivoted at angles relative to the rod 3 and pedicle screw assembly 8. In FIG. 12, it is shown that the pedicle screw assembly 8, can be in different positions relative to the spinal rod 3 and yet the spinal rod is properly aligned as demonstrated by the fact that the locking cap is in the locked position. The advantage of the present invention is illustrated by comparing FIG. 10 (Prior Art) and FIGS. 11 and 12 (present invention). In FIG. 10, the typical prior art pedicle assembly consists of a set screw and a washer. In the pedicle assembly of FIG. 10 (denoted as II), where the spinal rod does not align properly, the pedicle assembly cannot be properly assembled to secure the spinal rod. When the surgeon implants both pedicle screw assemblies, he cannot tell, using the prior art method and assembly that the rod is not in alignment. Unfortunately, the pedicle screw assembly of FIG. 10 (denoted as II), cannot pivot any further to compensate and thus allow the rod be secured in proper alignment.

Figure 8:
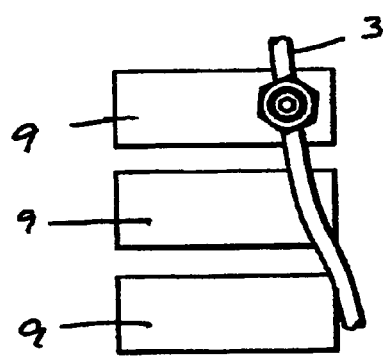
FIG. 8 is a schematic (representational) top view of a prior art pedicle screw assembly when implanted onto a vertebra, in which the spinal rod is misaligned.
Figure 9:
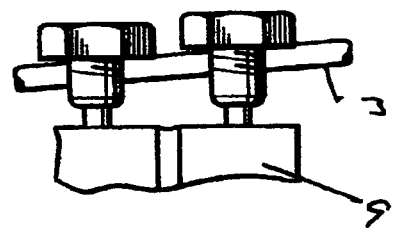
FIG. 9 is a schematic (representational) side view of prior art pedicle screw assemblies, demonstrating the mis-alignment of the spinal rod in prior art.

Similarly, FIG. 8 shows a schematic (representational) top view of a prior art pedicle screw assembly when implanted onto a vertebra 9, in which the spinal rod 3 is misaligned. FIG. 9 shows a schematic (representational) side view of prior art pedicle screw assemblies, demonstrating the misalignment of the spinal rod 3.

In the prior art, if the spinal rod is not aligned, the prior art relies on the polyaxial screw assembly to pivot to compensate for this lack of alignment. However, applicant notices that in practice, in the vast majority of surgeries, the pivot cannot compensate for the lack of alignment and as a result, the spinal rod remains unaligned, thus harming the patient. Applicant notices that in the majority of the cases, the angle of pivot (angle "A°") is not large enough to compensate for the spinal rod's lack of alignment. Thus, in the prior art, the spinal rod tends to be out of alignment, causing serious problems for the surgeon and the patient. Applicant also notices that, unfortunately, with the prior art system, the surgeon will not realize this lack of alignment, due to the bloody environment and obstructions of bodily parts which obscure the surgeon's manual access to and visual assessment of the spinal assemblies.

Thus, applicant provides the present invention which overcomes the lack of alignment and the deficiency of the prior art. With the present invention, the surgeon does not have to rely on the pivot which often fails to compensate for the mistake in alignment. The present invention allows a surgeon to easily and accurately ascertain that the spinal rod is aligned before finally fixing the pedicle screws into the vertebral bodies. The alignment of the spinal rod is assisted by the locking cap 1. The locking cap 1 is securely locked into position in both pedicle assemblies 8 (see e.g. FIG. 3), and this confirms to the surgeon that the spinal rod is aligned. As mentioned above, if the spinal rod is not aligned, the surgeon can determine by feel or by sight, that the locking cap 1 will not slide over body 5, or the locking cap 1 will not sit stably on body 5, or the locking cap 1 will not lock the spinal rod 3 and body 5 into position. The surgeon can then align the spinal rod by several means. For example, the surgeon can withdraw the spinal rod, and bend it appropriately, and re-insert it and quickly and easily re-test for alignment, using the locking cap 1 as a guide, until the locking cap 1 is securely locked into position which confirms to the surgeon that the spinal rod is aligned. Also, the surgeon can bend the spinal rod and adjust it along the interconnecting pedicle screw assemblies. Alternatively, the surgeon can readjust the position or location of one or more of the pedicle screw assemblies. Generally, the surgeon will bend the spinal rod, instead of performing the more difficult task of withdrawing the pedicle screw and re-inserting it in another location on the vertebra in order to adjust the spinal rod's alignment.

Thus, the invention ensures an alignment which hitherto has not been provided by the prior art. In contrast, in the prior art, even when the spinal rod is out of alignment and the pedicle screw assemblies cannot pivot any further to align the spinal rod, the spinal rod can still be threaded through the spinal rod passageway of the body, and thus the surgeon will not be able to determine that the spinal rod is out of alignment.

Additionally, even though polyaxial screws are made to pivot, and each is designed to have its maximum angle of pivot, it is not desirable for the polyaxial screw to pivot at too great an angle or even up to its maximum angle of "A°". For example, a polyaxial screw may have been designed to be capable of pivoting up to 15 degrees (that is, the maximum angle "A°", in FIG. 4E, is 15 degrees). However, in practice, it is preferable that the polyaxial screw only pivot up to 13 degrees. This is because a greater angle of pivot would put undue stress on the patient's vertebrae, and will also cause the interconnected pedicle screw assemblies to be less stable. Thus, the prior art which relies on the pivot of the polyaxial screw to compensate for the non-alignment of the spinal rod, will suffer from the disadvantages of the polyaxial screw pivoting at too great an angle. In contrast, the present invention locks the spinal rod into alignment, and locks the pedicle screw assemblies into position, and thus prevents the polyaxial screws from having to pivot (or pivoting) at too great an angle such as to put undue stress on the patient's vertebrae and to cause instability in the interconnected pedicle screw assemblies.

In short, the present invention allows the spinal rod 3 to be securely locked into alignment within each pedicle screw assembly 8, even if several interconnected pedicle screw assemblies 8 are used, for example, as shown in FIGS. 2, 3, 6, 7, 11 and 12. The present invention allows the surgeon to accomplish the foregoing quickly, easily and with less force, to the benefit of both the surgeon and patient.

It should be recognized that the present disclosure is not limited in any way to the illustrated pedicle screw, convex cup, and body. There exist in the prior art, different monoaxial pedicle screws, polyaxial pedicle screws, convex cups (washers), and bodies with a U-shaped slot having a passageway for the spinal rod—the foregoing may be used, with modifications to fit (e.g., as taught herein) with the presently disclosed locking cap and/or set screw. Further, different pedicle screws and bodies with a U-shaped slot having a passageway for the spinal rod may also be used in combination with the presently disclosed locking cap, set screw and convex cup. Also, other fasteners commonly utilized in spinal stabilization systems, for example screws such as monoaxial pedicle screws and polyaxial pedicle screws; hooks having alternative geometries; as well clamps plates, springs and wires are also envisioned. Indeed, it is envisioned that any component designed for attachment to an elongated spinal rod or transverse coupling spinal rod, may incorporate the locking cap of the subject disclosure, alone, or in combination with the presently disclosed set screw, convex cup, and/or body. Also, any number of fixation devices (fasteners) can be applied along the length of the spinal rod.

Having described preferred embodiments of the invention with reference to the accompanying drawings, it is to be understood that the embodiments shown herein are by way of non-limiting examples. It will be obvious that various modifications and changes which are within the skill of those skilled in the art are considered to fall within the scope of the present invention. Future technological advancements which allows for obvious changes in the basic invention herein are also within the scope of the present invention.

The invention claimed is:

1. A pedicle screw assembly comprising:
   a spinal rod;
   a body portion having a longitudinal passageway and a vertical interior bore, wherein the passageway is configured to receive and hold the spinal rod,
   a spinal fastener portion, which is configured to engage the spine and extends through the vertical interior bore of the body portion and through an opening in the lower end of the body portion corresponding to the vertical interior bore, and
   a locking cap configured to engage external surface of the body portion and to directly engage a lateral side of the spinal rod upon rotation of the locking cap relative to the body portion and spinal rod, wherein the locking cap and the passageway secure the spinal rod with a mechanical interlocking fit which secures the spinal rod perpendicular to the body portion when the locking cap is rotated about the body portion, and wherein the locking cap secures the spinal rod with a bayonet locking configuration comprising a channel cut into opposing sides of a lower portion of the locking cap with a flange at a lower end of the channel, wherein the channel is sized to receive the spinal rod, and wherein the flange directly engages the lateral side of the spinal rod, and the flange and the passageway secure the spinal rod with a mechanical interlocking fit when the locking cap is rotated in relationship to the body portion to secure the spinal rod perpendicular to the body portion.

2. The pedicle screw assembly of claim 1 wherein the flange and passageway are configured to secure the spinal rod at a 90° angle with respect to the vertical axis of the body portion.

3. The pedicle screw assembly of claim 1 wherein the body portion is cylindrical in shape.

4. The pedicle screw assembly of claim 1 wherein the passageway of the body portion is configured to receive the spinal rod that is cylindrical in shape.

5. The pedicle screw assembly of claim 1 wherein the fastener portion of the device for securing the spinal rod is selected from the group consisting of a screw, a hook, a clamp, a wire, a spring, a plate and a combination thereof.

6. The pedicle screw assembly of claim 1 wherein the fastener portion of the device is a pedicle screw.

7. The pedicle screw assembly of claim 1 wherein the fastener portion is a pedicle screw having a rounded or spherical upper head portion which will not pass through the opening in the lower portion of the body portion and a lower threaded portion for engagement of the spine or portions thereof.

8. The pedicle screw assembly of claim 1 wherein the fastener portion is a pedicle screw having a rounded or spherical upper head portion which will not pass through the opening in the lower portion of the body portion and a lower threaded portion for engagement of the spine or portions thereof.

9. The pedicle screw assembly of claim 7 wherein the upper head portion of the pedicle screw comprises a depression or opening for insertion of a drive device for driving the pedicle screw into a vertebra or other part of the spine of a patient.

10. The pedicle screw assembly of claim 6 wherein the pedicle screw is capable of pivotal movement relative to the body portion of the assembly.

11. The pedicle screw assembly of claim 10 wherein the pivotal movement is polyaxial movement with respect to the body portion and the polyaxial movement has a maximum angle of pivot of up to 26 degrees with respect to the central axis of the pedicle screw.

12. The pedicle screw assembly of claim 10 wherein pivotal movement is polyaxial movement with respect to the body portion and the polyaxial movement has a maximum angle of pivot which ranges from up to 11 to up to 26 degrees with respect to the central axis of the pedicle screw.

13. The pedicle screw assembly of claim 3 wherein the body portion has a U-shaped slot in opposing sides, sized to receive a spinal rod, and wherein the locking cap is cylindrical in shape and has a central bore which fits over the upper portion of the body portion and secures the spinal rod in the U-shaped slot in the body portion.

14. The pedicle screw assembly of claim 12 wherein the locking cap secures the spinal rod with a bayoneted locking configuration, the bayoneted locking configuration being a channel cut into opposing sides of a lower portion of the locking cap with a flange at a lower end of the channel, wherein the channel is sized to receive the spinal rod, and wherein the flange and channel engage the spinal rod with a mechanical interlocking fit when the locking cap is rotated about the central axis of the body portion such that the spinal rod is fixed with respect to the central axis of the body portion.

15. The pedicle screw assembly of claim 13, wherein the spinal rod is fixed at a 90° angle with respect to the vertical axis of the body portion.

16. The pedicle screw assembly of claim 13 wherein the assembly further includes, as a compression device, a set screw having external threads which are adapted to engage internal threads present in the body portion, and wherein the opening in the top portion of the locking cap will permit the set screw to pass there through, and wherein the set screw passes threadably through the vertical interior bore of the body portion to engage the spinal rod that is in the U-shaped slot, wherein the compression by the set screw holds the pedicle screw assembly fixedly in place.

17. The pedicle screw assembly of claim 13 further comprising a convex cap, wherein the convex cap is sized to fit within the vertical interior bore of the body portion, rests on the enlarged head of the pedicle screw seated in the lower portion of the body portion, and wherein the spinal rod in the U-shaped slot in the upper portion of the body portion rests on top of the convex cap, such that when the set screw compresses the spinal rod, the spinal rod is compressed against the convex cap which in turn is compressed against the enlarged upper portion of the pedicle screw, wherein the compression by the set screw holds the pedicle screw assembly fixedly in place.

18. A pedicle screw assembly, comprising: a locking cap, a spinal rod, a fastener, a set screw and a body, wherein the locking cap is configured to secure the spinal rod in the body of the pedicle screw assembly and wherein the body contains an axial bore for receiving the fastener and a passageway through which the spinal rod passes or in which it rests, said locking cap is configured to slide over the body, once the spinal rod is in place in the body, with the ends of the spinal rod extending beyond the body, the locking cap secures the spinal rod with a bayoneted locking configuration, the bayoneted locking configuration being a channel cut into opposing sides of a lower portion of the locking cap with a flange at a lower end of the channel, wherein the channel is sized to receive the spinal rod, and wherein the flange directly engages a lateral side of the spinal rod, and the flange and the passageway secure the spinal rod with a mechanical interlocking fit which secures the spinal rod perpendicular to the body when the locking cap is rotated about the central axis of the body.

19. The locking cap of claim 18, wherein the spinal rod passageway in the body is a U-shaped slot.

20. The locking cap of claim 18, wherein the body is provided with a vertical interior bore, and the vertical interior bore in the body is threaded to receive the set screw, and the locking cap has an opening in the top portion, wherein the opening in the top portion of the locking cap will permit the set screw to pass there through, and wherein the set screw passes threadably through the vertical interior bore of the body to engage the spinal rod thereby compressing the spinal rod onto an enlarged upper portion of a fastener which is seated in a lower portion of the vertical interior bore of the body, wherein the compression by the set screw holds the locking cap, spinal rod, fastener and body of the pedicle screw assembly fixedly in place.

21. A pedicle screw assembly, comprising: a locking cap, a spinal rod, a fastener, a set screw and a body, wherein the locking cap is configured to secure the spinal rod in the body, wherein the body is cylindrical in shape with a longitudinal central passageway and with a vertical interior bore there through, and wherein the body has a U-shaped slot in opposing sides of an upper portion wherein the U-shaped slot is sized to receive a spinal rod, and wherein the locking cap is cylindrical in shape and has a central bore which fits over the upper portion of the body and secures the spinal rod in the U-shaped slot in the body, wherein the locking cap secures the spinal rod with a bayoneted locking configuration, the bayoneted locking configuration being a channel cut into opposing sides of a lower portion of the locking cap with a flange at a lower end of the channel, wherein the channel is sized to receive the spinal rod, and wherein the flange directly engages a lateral side of the spinal rod, and the flange and the U-shaped slot secure the spinal rod with a mechanical interlocking fit which secures the spinal rod perpendicular to the body when the locking cap is rotated about the central axis of the body, and wherein the vertical interior bore of the body is threaded to receive a set screw which is threaded to mate with the threaded vertical interior bore in the upper portion of the body, and the locking cap has an opening in a top portion, wherein the opening in the top portion of the locking cap will permit the set screw to pass there through, and wherein the set screw passes threadably through the vertical interior bore of the body to engage the spinal rod thereby compressing the spinal rod onto an enlarged upper portion of a fastener which is seated in a lower portion of the vertical interior bore of the body, wherein the compression by the set screw holds the locking cap, spinal rod, fastener and body of the pedicle screw assembly fixedly in place.

22. A method of spinal stabilization comprising:
attaching, to the spine or vertebrae of a patient in need thereof, a pedicle screw assembly for securing or fixing a spinal rod along a portion of the spine, wherein the pedicle screw assembly comprises a body portion with a central axis and a vertical interior bore wherein the body portion further includes a spinal rod passageway which is configured to receive and hold a spinal rod, a locking cap configured to engage the body portion wherein the spinal rod rests, a fastener portion, which extends through the body portion through an opening in the lower end thereof and is configured to engage the spine, wherein the locking cap directly engages external surface of the body portion and a lateral side of the spinal rod upon rotation of the locking cap relative to the body portion which secures the spinal rod perpendicular to the body portion;
receiving the spinal rod in the spinal rod passageway; and
engaging the locking cap on the body portion, and rotating the locking cap relative to the body portion, thereby securing the position of the spinal rod perpendicular to the body portion by a mechanical interlocking fit between the locking cap and the passageway, wherein the locking cap secures the spinal rod with a bayoneted locking configuration, the bayoneted locking configuration being a channel cut into opposing sides of a lower portion of the locking cap with a flange at a lower end of the channel, wherein the channel is sized to receive the spinal rod, and wherein the flange and channel engage the spinal rod with a mechanical interlocking fit when the locking cap is rotated about the central axis of the body portion such that the spinal rod is fixed with respect to the central axis of the body portion and is engaged by placing the locking cap over the body portion and turning the locking cap to lock the spinal rod within the body portion.

23. The method of claim 22 wherein the fastener portion is selected from the group consisting of a screw, a hook, a clamp, a wire, a spring, a plate and a combination thereof.

24. The method of claim 22, wherein the fastener portion is a pedicle screw.

25. The method of claim 22 wherein the body portion is cylindrical in shape.

26. The method of claim 25 wherein the spinal rod is fixed at a 90° angle with respect to the vertical axis of the body portion.

* * * * *